United States Patent [19]

Wilk et al.

[11] Patent Number: 5,490,507
[45] Date of Patent: Feb. 13, 1996

[54] METHOD AND APPARATUS FOR GENERATING PELVIC MODEL

[76] Inventors: Peter J. Wilk, 185 W. End Ave., New York, N.Y. 10023; Mitchell N. Essig, 227 High Brook Ct., Pelham, N.Y. 10803

[21] Appl. No.: 200,752

[22] Filed: Feb. 23, 1994

[51] Int. Cl.⁶ ............................ A61B 5/055; A61B 6/03; A61B 17/42; G09B 23/30
[52] U.S. Cl. ............................ 128/653.1; 128/653.2; 128/778; 128/775; 434/267; 434/272; 434/273
[58] Field of Search ............................ 128/653.1, 653.2, 128/774, 775, 778; 364/413.13, 413.14; 623/66; 434/267, 273, 272

[56] References Cited

U.S. PATENT DOCUMENTS

| | | | |
|---|---|---|---|
| 2,132,226 | 10/1938 | Wahlberg | 434/267 |
| 3,921,311 | 11/1975 | Beasley et al. | 434/267 |
| 4,337,186 | 6/1982 | Crisp et al. | 525/362 |
| 4,436,684 | 3/1984 | White | 128/653.1 |
| 4,481,001 | 11/1984 | Graham et al. | 434/267 |
| 4,681,547 | 7/1987 | Herron | 434/273 |
| 4,841,975 | 6/1989 | Woolson | 128/653.1 |
| 5,312,669 | 5/1994 | Bedard | 623/33 |

*Primary Examiner*—Krista M. Zele
*Attorney, Agent, or Firm*—R. Neil Sudol; Henry D. Coleman

[57] ABSTRACT

A medical method comprises the steps of scanning a female patient in a pelvic region to obtain electrically encoded data specifying the patient's pelvic structure, stacking a series of transparent sheets, and during the step of stacking, depositing a hardenable opaque liquid substance on the sheets in accordance with the electrically encoded data to form a three-dimensional model of the patient's pelvic structure. Also during the step of stacking, the liquid substance is subjected, upon deposition thereof on the sheets, to an energy tending to cure the liquid substance. The sheets are bonded to one another to form a substantially unitary body incorporating the model.

20 Claims, 1 Drawing Sheet

5,490,507

METHOD AND APPARATUS FOR GENERATING PELVIC MODEL

BACKGROUND OF THE INVENTION

This invention relates to a medical technique and an associated device for use in performing the method. More particularly, this invention relates to a method and apparatus for generating a model of a patient's pelvis.

Generally, most women have a sufficiently large pelvis to accommodate the birth of an infant, provided that the infant is properly positioned for its birth. It frequently occurs, however, that the infant is not properly positioned. To determine whether a Cesarean section is necessary, a physician must conclude from the position of the infant and a general estimate of the pregnant woman's size that difficulty may or will be encountered during birth. This determination is not precise Consequently, many more women than necessary are subjected to Cesarean birth.

OBJECTS OF THE INVENTION

An object of the present invention is to provide a method for facilitating the diagnosis of a pregnant woman to determine the necessity of Cesarean section.

Another object of the present invention is to provide a method for generating a model of a pregnant woman's pelvis.

Another, more particular, object of the present invention is to provide such a method which is quick and easy to perform.

A further object of the present invention is to provide a device for implementing the method.

These and other objects of the present invention will be apparent from the drawings and detailed descriptions herein.

SUMMARY OF THE INVENTION

A method for use in medical diagnosis and treatment comprises, in accordance with the present invention, the steps of scanning a female patient in a pelvic region to obtain electrically encoded data specifying the patient's pelvic structure and, in accordance with the electrically encoded data, depositing a hardenable opaque liquid substance on a series of transparent sheets such that, upon a stacking of the sheets and a hardening of the liquid substance, a three-dimensional model of the patient's pelvic structure is generated. In further steps of the method, the liquid substance is subjected, upon deposition thereof on the sheets, to an energy tending to cure the liquid substance, the sheets are stacked and bonded to one another to form a substantially unitary body incorporating the model.

According to another feature of the present invention, the method further comprises the step of cutting the sheets, upon deposition of the liquid substance thereon and upon a stacking of the sheets, to remove excess sheet material and to conform the sheets to the model. The sheets may be cut together, upon completed stacking thereof and upon formation of the model. Alternatively, each sheet may be cut individually prior to or subsequently to the placement of the individual sheet on the stack and prior to or subsequently to the deposition of the liquid modeling substance on the sheets.

It is to be noted that cutting of the sheets is not necessary, insofar as certain benefits may be obtained by observing the model through the transparent sheet material.

The energy used to cure the deposited liquid substance may be ultraviolet radiation or, for example, ultrasonic pressure waves.

The scanning step may be implemented by operating a nuclear magnetic resonance imaging apparatus or a computer aided tomography scanning apparatus.

According to another feature of the present invention, the liquid substance is deposited on a sheet and subjected to the energy prior to a placement of another sheet on the stack of sheets, thereby forming the model as a series of slices. Alternatively, the liquid substance may be deposited on the sheets separately, prior to deposition thereof on the stack of sheets. This alternative permits the formation of several slices substantially simultaneously and reduces the total time required to complete the model.

The sheets may be bonded to one another with an adhesive. To that end, each sheet may be precoated with a layer of adhesive material to facilitate the model generation process. The sheets need only be pressed together to achieve bonding.

According to a further feature of the present invention, the scanning is performed in a first location and the steps of depositing, subjecting, stacking and bonding are performed in a second location remote from the first location. The method then further comprises the step of wirelessly transmitting the electrically encoded data from the first location to the second location.

Where the patient is pregnant, the method further comprises the step of using the model, upon formation thereof, to determine whether the patient is to give birth in a Cesarean operation.

A medical method comprises, in accordance with a particular embodiment of the present invention, the steps of (a}) scanning a female patient in a pelvic region to obtain electrically encoded data specifying the patient's pelvic structure, (b}) stacking a series of transparent sheets, and (c}) during the step of stacking, depositing a hardenable opaque liquid substance on the sheets in accordance with the electrically encoded data to form a three-dimensional model of the patient's pelvic structure. Also during the step of stacking, the liquid substance is subjected, upon deposition thereof on the sheets, to an energy tending to cure the liquid substance. The sheets are bonded to one another to form a substantially unitary body incorporating the model.

As discussed above, the method may further comprise the step of cutting the sheets, upon deposition of the liquid substance thereon and upon a stacking of the sheets, to remove excess sheet material and to conform the sheets to the model.

A medical device comprises, in accordance with the present invention, a scanner for generating electrically encoded data pertaining to a patient's pelvic structure, a stacker for stacking a series of transparent sheets, a deposition or placement component for depositing a hardenable opaque liquid substance on the sheets, a curing element juxtaposed to the sheets for exposing the liquid substance, upon deposition thereof on the sheets, to a curing energy, and a control unit operatively connected to the scanner, the deposition component and the stacker for sequencing the deposition of the liquid substance on the sheets and the stacking of the sheets in conformity with the electrically encoded data from the scanner to generate a three-dimensional model of the pelvic structure of the patient.

According to another feature of the present invention, the control unit is operatively connected to scanner via a wireless communications link. Thus, the pelvic structure of a patient in one location may be examined by a physician in another location. This operating option is useful, for example, where multiple opinions are necessary or desirable or where the patient's personal physician is at a distance.

The stacker and the deposition component may be juxtaposed to one anther and controlled by the control unit to deposit the liquid substance on any individual one of the sheets only upon placement of the sheet on top of the stack.

According to an additional feature of the present invention, the model generating device further comprises a cutter operatively connected to the control unit for removing excess material from the sheets, upon deposition of the liquid substance thereon and upon a stacking of the sheets, to conform the sheets to the model.

A method and device in accordance with the present invention provides the gynecologist or obstetrician with easily appreciated information in the form of a physical (life-size) model of a patient's pelvis. This greatly facilitates the determination of whether a patient should be subjected to a Cesarean section. The determination is more accurate than conventional speculative techniques and accordingly saves many women the trauma of unnecessary surgery while also ensuring that when rewired the surgical procedure will be performed.

DETAILED DESCRIPTION

Figure 1:
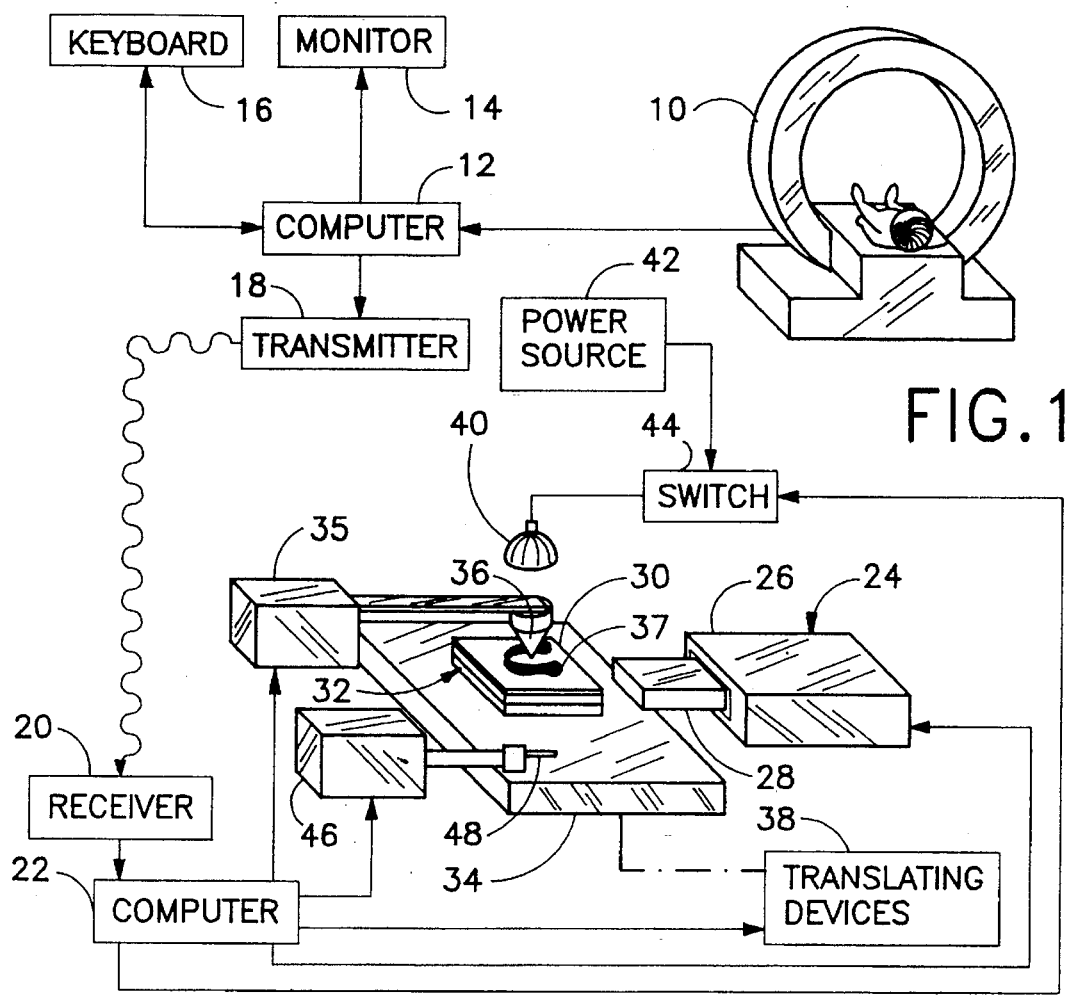
FIG. 1 is a block diagram of a model generating system or device in accordance with the present invention.

As illustrated in FIG. 1, a system or device for generating a model of a women's pelvis for facilitating obstetrical diagnosis and treatment comprises a computer aided tomography (CAT) or magnetic resonance imaging (MRI) scanner 10 for generating electrically encoded data pertaining to a pelvic structure of a patient P. Scanner 10 includes or is connected to a local computer 12 which controls the generation and organization of the structural data. Computer 12 is coupled to a monitor 14 for displaying the results of a scanning operation and to a keyboard 16. Keyboard 16 provides instructions to computer 12, for example, for wirelessly transmitting the electrically encoded pelvic structural data via a transmitter 18 and a receiver 20 to a remote computer 22. Computer 22 controls the production of a physical model of the patient's pelvis in accordance with the electrically encoded structural data from computer 12.

Computer 22 is connected to a stacker 24 which includes a housing 26 and a shiftable vacuum manifold tray 28. Tray 28 lifts sheets 30 of transparent polymeric material and deposits them in a stack 32 on a carriage or table 34. Computer 22 controls or times the operation of tray 28. Computer 22 is also connected to a deposition component 34 which includes a nozzle 36 for depositing a hardenable opaque liquid substance 37 on successive sheets 30 upon the placement thereof in stack 32. The pattern in which the liquid substance is deposited on each sheet 30 is controlled by computer 22 in accordance with the information received from scanner 10 and computer 12. Computer 22 and carriage 34 are operatively coupled to a plurality of linear of translating drives 38 and possibly rotary drives (not separately illustrated) for moving carriage 34 in accordance with numerical control data.

As further illustrated in FIG. 1, a curing element in the form of an ultraviolet lamp 40 is connected to a power source 42 via a switch 44 which is opened and closed by computer 22. Ultraviolet lamp 40 is juxtaposed or juxtaposable to sheets 30 in stack 32 for exposing the liquid substance 37, upon deposition thereof on sheets 30, to ultraviolet radiation for purposes of curing or hardening the deposited liquid material.

Computer 22 sequences the deposition of liquid substance 37 on sheets 30 and the stacking of sheets 30 by stacker 24 in conformity with the electrically encoded data from scanner 10 and computer 12 to generate a three-dimensional pelvic model in the form of hardened liquid 37. Liquid 3 is deposited on sheets 30 in patterns determined by numerical control data from scanner 10 and computer 12. Each sheet 30 represents a thin slice of the patient's pelvis.

As additionally illustrated in FIG. 1, computer 22 is operatively connected to a cutter machine 46 including a drill or laser tip 48 or other cutting element. Computer 22 operates cutter machine 46 and drives 38 to remove excess material from sheets 30, around the model, upon deposition of liquid substance 37 on sheets 30 and upon a stacking of the sheets. This removal of material in effect shapes stack 32 to conform to the pelvic model.

Figure 2:
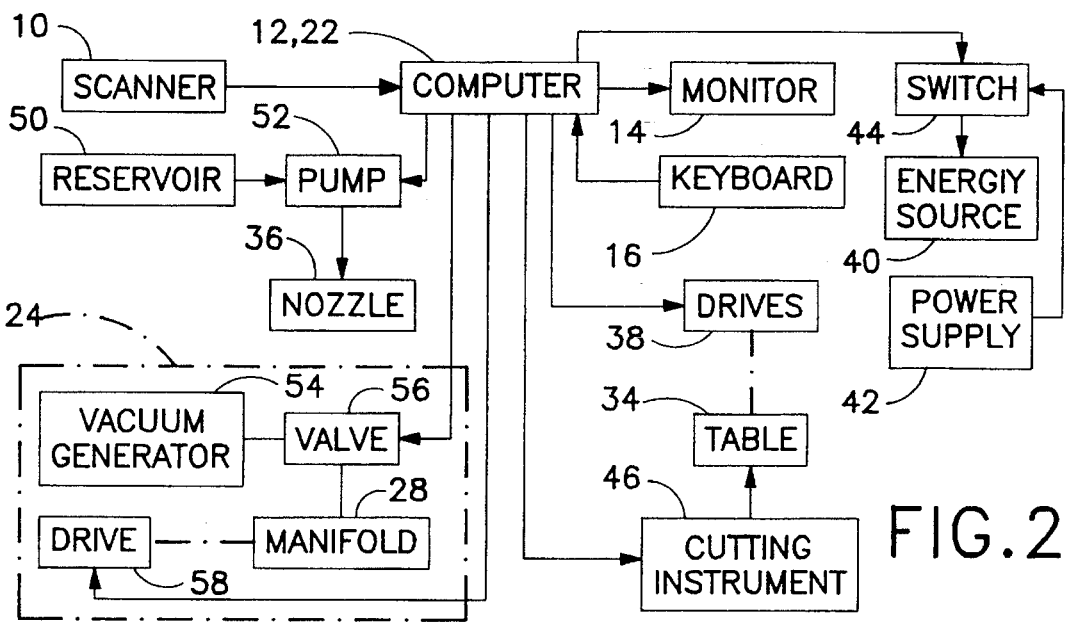
FIG. 2 is another block diagram of the system or device of FIG. 1 with modifications.

In FIG. 2, those elements of the model generating apparatus which correspond in structure and function to the elements in FIG. 1 are labeled with the same reference designations. In the modified embodiment of FIG. 2, the wireless communications link represented by transmitter 18 and receiver 20 are eliminated, while a liquid reservoir 50 and a pump 52 of deposition component 34 are diagrammatically shown. Pump 52 communicates with reservoir 50 and nozzle 36 and is operatively tied to computer 22 for moving liquid from the reservoir to the nozzle in response to signals from the computer. FIG. 2 also shows additional elements of stacker 24, namely, a vacuum generator 54, a valve 56 and a drive 58. Valve 56 is connected to manifold tray 28 and computer 22 for evacuating air from the manifold tray at times determined by computer 22. Computer 22 controls drive 58 to shift manifold tray 28 in and out and, optionally, up and down, depending on the size of stack 32.

It is to be noted that other arrangements of a model generating device are possible to implement a modified method. For example, several liquid deposition components may be associated with one or more stackers, whereby the formation of a model may be facilitated by parallel operations.

It is to be noted further that an ultrasonic pressure wave source (not illustrated) may be disposed proximately to carriage 34 for use in facilitating or inducing the curing of liquid substance 37. An ultrasonic pressure wave generator may also serve to bond sheets 30 to one another to form stack 32 as a unitary body. Alternatively, sheets 30 may be precoated with a layer of adhesive material for bonding the sheets together prior to cutting by machine 46. In that case, stacker 24 includes means for separating sheets 30 from protective cover or backing layers (not shown). Alternatively, sheets 30 may be coated with a bonding material.

In another bonding alternative method, an adhesive application device such as a spray nozzle is juxtaposed to carriage 34 and operatively connected to computer 22 for applying adhesive to an uppermost sheet 30 in stack 32. The adhesive may be selected so as to be curable by ultraviolet radiation.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for use in medical diagnosis and treatment, comprising the steps of:

scanning a female patient in a pelvic region to obtain electrically encoded data specifying the patient's pelvic structure;

in accordance with said electrically encoded data, depositing a hardenable opaque liquid substance on a series of transparent sheets such that, upon a stacking of said sheets and a hardening of said liquid substance, a three-dimensional model of the patient's pelvic structure is generated;

subjecting said liquid substance, upon deposition thereof on said sheets, to an energy tending to cure said liquid substance;

stacking said sheets; and bonding said sheets to one another to form a substantially unitary body incorporating said model.

2. The method defined in claim 1, further comprising the step of cutting said sheets, upon deposition of said liquid substance thereon and upon a stacking of said sheets, to remove excess sheet material and to conform said sheets to said model.

3. The method defined in claim 2 wherein said step of cutting is implemented only upon a stacking of all of said sheets.

4. The method defined in claim 2 wherein said step of cutting is implemented for each sheet separately, upon a deposition of said liquid substance on such sheet.

5. The method defined in claim 1 wherein said energy is ultraviolet radiation.

6. The method defined in claim 1 wherein said energy is ultrasonic pressure waves.

7. The method defined in claim 1 wherein said step of scanning includes the step of operating a nuclear magnetic resonance imaging apparatus.

8. The method defined in claim 1 wherein said step of scanning includes the step of operating a computer aided tomography scanning apparatus.

9. The method defined in claim 1 wherein said liquid substance is deposited on a sheet and subjected to said energy prior to a placement of another sheet on said stack of sheets, thereby forming said model as a series of slices.

10. The method defined in claim 1 wherein said step of bonding includes the step of applying an adhesive to said sheets.

11. The method defined in claim 1 wherein said sheets are provided with a predeposited layer of adhesive, said step of bonding including the step of pressing said sheets together upon stacking thereof so that said adhesive connects said sheets to one another.

12. The method defined in claim 1 wherein said step of scanning is performed in a first location and said steps of depositing, subjecting, stacking and bonding are performed in a second location remote from said first location, further comprising the step of wirelessly transmitting said electrically encoded data from said first location to said second location.

13. The method defined in claim 1 wherein the patient is pregnant, further comprising the step of using said model, upon formation thereof, to determine whether the patient is to give birth in a Cesarean operation.

14. A medical device comprising:

scanning means for generating electrically encoded data pertaining to a patient's pelvic structure;

stacking means for stacking a series of transparent sheets;

deposition means for depositing a hardenable opaque liquid substance on said sheets;

curing means juxtaposed to said sheets for exposing said liquid substance, upon deposition thereof on said sheets, to a curing energy; and control means operatively connected to said scanning means, said deposition means and said stacking means for sequencing the deposition of said liquid substance on said sheets and the stacking of said sheets in conformity with said electrically encoded data from said scanning means to generate a three-dimensional model of said pelvic structure of the patient.

15. The device defined in claim 14 wherein said control means is operatively connected to said scanning means via a wireless communications link.

16. The device defined in claim 14 wherein said stacking means and said deposition means are juxtaposed and controlled by said control means to deposit said liquid substance on any individual one of said sheets only upon placement of said sheet on top of said stack.

17. The device defined in claim 14, further comprising cutting means operatively connected to said control means for removing excess material from said sheets, upon deposition of said liquid substance thereon and upon a stacking of said sheets, to conform said sheets to said model.

18. A medical method, comprising the steps of:

scanning a female patient in a pelvic region to obtain electrically encoded data specifying the patient's pelvic structure;

stacking a series of transparent sheets;

during said step of stacking, depositing a hardenable opaque liquid substance on said sheets in accordance with said electrically encoded data to form a three-dimensional model of the patient's pelvic structure;

also during said step of stacking, subjecting said liquid substance, upon deposition thereof on said sheets, to an energy tending to cure said liquid substance; and bonding said sheets to one another to form a substantially unitary body incorporating said model.

19. The method defined in claim 18, further comprising the step of cutting said sheets, upon deposition of said liquid substance thereon and upon a stacking of said sheets, to remove excess sheet material and to conform said sheets to said model.

20. The method defined in claim 18 wherein the patient is pregnant, further comprising the step of using said model, upon formation thereof, to determine whether the patient is to give birth in a Cesarean operation.

* * * * *